US009170191B2

(12) United States Patent
Coffin et al.

(10) Patent No.: US 9,170,191 B2
(45) Date of Patent: Oct. 27, 2015

(54) MOTORIZED VARIABLE PATH LENGTH CELL FOR SPECTROSCOPY

(71) Applicants: John Magie Coffin, Blue Mounds, WI (US); Damian W. Ashmead, Belleville, WI (US); Todd C. Strother, Cottage Grove, WI (US)

(72) Inventors: John Magie Coffin, Blue Mounds, WI (US); Damian W. Ashmead, Belleville, WI (US); Todd C. Strother, Cottage Grove, WI (US)

(73) Assignee: Thermo Electron Scientific Instruments LLC, Madison, WI (US)

(*) Notice: Subject to any disclaimer, the term of this patent is extended or adjusted under 35 U.S.C. 154(b) by 0 days.

(21) Appl. No.: 13/931,348

(22) Filed: Jun. 28, 2013

(65) Prior Publication Data
US 2014/0008539 A1      Jan. 9, 2014

Related U.S. Application Data

(60) Provisional application No. 61/669,254, filed on Jul. 9, 2012.

(51) Int. Cl.
*H01L 37/00* (2006.01)
*G01N 21/25* (2006.01)
*G01N 21/03* (2006.01)

(52) U.S. Cl.
CPC .......... *G01N 21/255* (2013.01); *G01N 21/0303* (2013.01)

(58) Field of Classification Search
CPC .......... G01N 21/3563; G01N 21/3577; G01N 21/0303; G01N 21/3504; G01N 21/39; G01N 2021/154; G01N 2021/3181; G01N 21/21; G01N 21/255; G01N 21/35; G01N 21/552; G01N 2201/0624

USPC ...................................................... 250/338.2
See application file for complete search history.

(56) References Cited

U.S. PATENT DOCUMENTS

| 4,784,487 | A | * | 11/1988 | Hopkins et al. | ............... 356/326 |
| 5,223,715 | A | | 6/1993 | Taylor | |
| 6,042,785 | A | * | 3/2000 | Harju | ............... 422/52 |
| 7,365,852 | B2 | | 4/2008 | Schleifer | |
| 7,581,435 | B2 | | 9/2009 | Pelletier | |

(Continued)

FOREIGN PATENT DOCUMENTS

EP         1 792 653 B1      11/2007

OTHER PUBLICATIONS

Axiom Analytical Incorporated, "FST-500 Uniprobe Sample Stage—A universal fiber-optic sampling accessoty for liquids and solids in any form," Data Sheet, 2 pages, http://www.goaxiom.com/pdf/Data_Sheets/PS_FST_03(401).pdf.

*Primary Examiner* — David J Makiya
*Assistant Examiner* — Taeho Jo
(74) *Attorney, Agent, or Firm* — Ion C. Abraham

(57) ABSTRACT

The present invention is thus directed to an automated system and method of varying the optical path length in a sample that a light from a spectrophotometer must travel through. Such arrangements allow a user to easily vary the optical path length while also providing the user with an easy way to clean and prepare a transmission cell for optical interrogation. Such path length control can be automatically controlled by a programmable control system to quickly collect and stores data from different path lengths as needed for different spectrographic analysis. Such a methodology and system, as presented herein, is able to return best-match spectra with far fewer computational steps and greater speed than if all possible combinations of reference spectra are considered.

2 Claims, 2 Drawing Sheets

(56) References Cited

U.S. PATENT DOCUMENTS

| | | |
|---|---|---|
| 7,582,869 B2 | 9/2009 | Sting et al. |
| 8,189,199 B2 | 5/2012 | Robertson, Jr. et al. |
| 2002/0060791 A1* | 5/2002 | Stumbo et al. ............... 356/317 |
| 2003/0023152 A1* | 1/2003 | Abbink et al. ............... 600/316 |
| 2008/0017799 A1* | 1/2008 | Sting et al. ............... 250/339.01 |
| 2009/0290153 A1* | 11/2009 | Juhl ............................. 356/319 |
| 2010/0085568 A1* | 4/2010 | Robertson et al. ............ 356/319 |
| 2010/0085571 A1* | 4/2010 | Robertson et al. ............ 356/432 |
| 2011/0149280 A1 | 6/2011 | Juhl |
| 2011/0244479 A1* | 10/2011 | Schultz et al. ................. 435/7.1 |
| 2012/0122084 A1* | 5/2012 | Wagner et al. ................. 435/6.1 |
| 2012/0127470 A1* | 5/2012 | Chumachenko et al. ..... 356/440 |
| 2012/0301917 A1* | 11/2012 | Mossoba et al. ................. 435/38 |
| 2012/0320375 A1* | 12/2012 | Lipson et al. ................. 356/246 |

* cited by examiner

MOTORIZED VARIABLE PATH LENGTH CELL FOR SPECTROSCOPY

BACKGROUND OF THE INVENTION

1. Field of the Invention

The present invention relates to the field of spectral analysis and, more specifically, toward the identification of the type and quantity of different chemicals in solid (e.g., soft) and liquid samples by transmitting light of varying wavelengths through the sample so as to provide wavelength information and to provide measured amounts of light absorbed by any given sample.

2. Discussion of the Related Art

A molecular spectrometer is an instrument wherein a solid, liquid, or gaseous sample is illuminated, often with nonvisible light such as light in the infrared region of the spectrum. The light transmitted through the sample is then captured and analyzed to reveal information about the characteristics of the sample. As an example, a sample may be illuminated with infrared light having a known intensity across a range of wavelengths, and the light transmitted by the sample can then be captured for comparison to the light source. Review of the captured spectra can then illustrate the wavelengths at which the illuminating light was absorbed by the sample. The spectrum, and in particular the locations and amplitudes of the peaks therein, can be compared to libraries of previously obtained reference spectra to obtain information about the sample, such as its composition and characteristics. In essence, the spectrum serves as a "fingerprint" for the sample and for the substances therein, and by matching the fingerprint to one or more known fingerprints, the identity and the quantity of the sample might be determined.

However, there are numerous occasions when the data collected using such above described methods is useless because the transmitted light is substantially absorbed by too large of a path length, or the light is nearly totally transmitted by too small of path length. Either one of these situations can be problematic. With respect to a large absorbance (e.g., due to a large path length), uncertainties based on noise (i.e., signal-to-noise) become problematic as the spectral signal of the sample is lost due to the light being too weak to be reliably detected within a larger signal. However, if the absorbance signal is too small (e.g., due to a small path length), reliable detection is still a problem also because of a lack of absorbance signal strength even though overall light level is high. By varying the path length through the sample, both of these problems can be minimized. Other uncertainties in both situations also can include natural variations in the light intensity caused by dirt, dust in the light beam, temperature, vibration variations affecting the measurement means, and/or finally statistical variation the light source and detection system.

Background information on an apparatus and methodology that provides for measuring optimized absorbance properties of a liquid droplet can be found in U.S. Pat. No. 7,365,852, to Schleifer, issued Apr. 29, 2008, entitled; "Methods and Systems for Selecting Pathlength in Absorbance Measurements," including the following: "[m]ethods and subsystems for substantially optimizing the absorbance measurement in optical instruments are provided. A method comprises forming a liquid sample into a droplet extending between opposing surfaces, passing a light beam through the sample, and varying the distance between the two opposing surfaces until a distance substantially corresponding to a optimum absorbance is obtained."

Background information on an apparatus and methodology that provides for measuring transmission properties of liquids and solids can be found in U.S. Pat. No. 7,582,869, to Sting et al., issued Sep. 1, 2009, entitled; "System and Method for Optical Analysis," including the following: "[a]n optical analysis system utilizing transmission spectroscopy for analyzing liquids and solids includes a source of optical energy, a sample, a movable optical energy transmission window, a fixed optical energy transmission window, and a detection system. The fixed transmission window remains fixed relative to the source of optical energy. The sample is selectively positioned between the movable and fixed optical energy transmission windows for analyzing the sample. The optical energy is transmitted through one of the windows, the sample, and the other window to obtain encoded optical energy as a result of transmitting the optical energy through the sample. A detection system receives the encoded optical energy for analysis. The movable optical energy transmission window is selectively movable relative to the fixed optical energy transmission window to repeatedly and precisely align and make readily accessible both windows and the sample."

Background information on an apparatus and methodology that provides for measuring transmission properties of compressed samples can be found in EP 1, 792, 653, to Juhl, issued Jun. 6, 2006, entitled; "Apparatus and method for spectrophotometric analysis," including the following: "[a]n apparatus for spectrophotometric analysis comprises a sample reception surface, which is arranged to receive a sample to be analysed, and a sample contacting surface, which is moveable in relation to the sample reception surface such that it may be brought to a first position, where the surfaces are sufficiently far apart to allow the sample to be placed on the sample reception surface, and a second position, where the sample contacting surface makes contact with the sample and compresses the sample. The apparatus further comprises a sample thickness controller, which is arranged to control the distance between the sample reception surface and the sample contacting surface in the second position of the sample contacting surface, such that a sample thickness between the surfaces may be shifted for obtaining at least two measurements of the sample at different optical path lengths through the sample."

SUMMARY OF THE INVENTION

The present invention is directed to an automated system and method of varying the optical path length in a sample that a light from a spectrophotometer must travel through. In particular, the present embodiments described herein allow the user to easily vary the optical path length over a large range typically from about 10 microns to about 1000 microns while providing the user with an easy way to clean and prepare a transmission cell for optical interrogation. Such varied path lengths can be automatically manipulated by a programmable control system to quickly collect and store data from different path lengths as needed for different spectrographic analysis.

Thus, an aspect of the present application includes an apparatus for measuring an optical property of a sample that includes: a source of optical energy; a first and a second window; the first window configured to receive directed optical energy from the source over free space and wherein both the first and the second windows are moveable with respect to the positioning of the source of optical energy, and wherein the first window is optically coupled to the second window; a processor; and means for adjusting a separation between configured surfaces of the first and second window surfaces at a variable distance (P) to pull a sample into a column so as to be contained by surface tension or to squeeze the sample during optical analysis of the sample, wherein the processor is configured to collect and store many data sets of different optical path lengths automatically of the pulled and/or squeezed sample.

Another aspect of the present application includes a method for measuring an optical property of a sample, that includes: providing a pair of windows; wherein one of the pair of windows is configured to receive radiation from a source of optical energy over free space and the other of the pair of windows is configured with an incorporated optical detector that is utilized to optically interrogate a disposed sample therebetween the pair of windows, wherein the pair of windows are both moveable with respect to the positioning of the source of optical energy; and providing a processor adapted to control a separation between configured surfaces of the pair of windows at a variable distance (P) in order to pull the disposed sample into a column contained by surface tension or to squeeze the sample during optical analysis, wherein the processor is additionally configured to collect and store information of different optical path lengths automatically of the pulled and/or squeezed sample(s).

DETAILED DESCRIPTION

Figure 1:
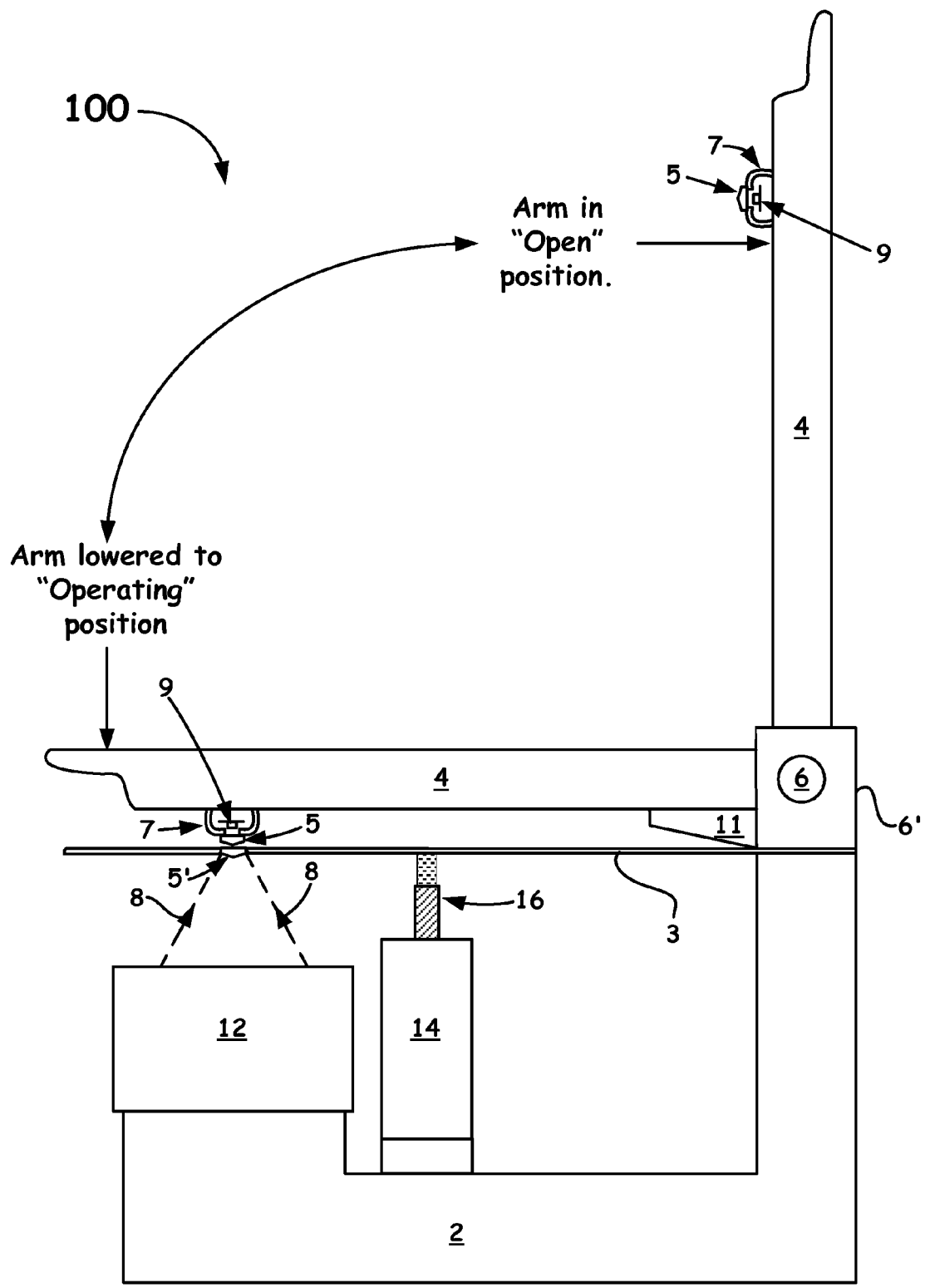
FIG. 1 shows an exemplary infrared (IR) system.

In the description of the invention herein, it is understood, that a word appearing in the singular encompasses its plural counterpart, and a word appearing the plural encompasses its singular counterpart, unless implicitly or explicitly understood or stated otherwise. Furthermore, it is understood that for any given component or embodiment described herein, any of the possible candidates or alternatives listed for that component may generally be used individually or in combination with one another, unless implicitly or explicitly understood or stated otherwise. Moreover, it is to be appreciated that the figures, as shown herein, are not necessarily drawn to scale, wherein some of the elements may be drawn merely for clarity of the invention. Also, reference numerals may be repeated among the various figures to show corresponding or analogous elements. Additionally, it will be understood that any list of such candidates or alternatives is merely illustrative, not limiting, unless implicitly or explicitly understood or stated otherwise. In addition, unless otherwise indicated, numbers expressing quantities of ingredients, constituents, reaction conditions and so forth used in the specification and claims are to be understood as being modified by the term "about."

Accordingly, unless indicated to the contrary, the numerical parameters set forth in the specification and attached claims are approximations that may vary depending upon the desired properties sought to be obtained by the subject matter presented herein. At the very least, and not as an attempt to limit the application of the doctrine of equivalents to the scope of the claims, each numerical parameter should at least be construed in light of the number of reported significant digits and by applying ordinary rounding techniques. Notwithstanding that the numerical ranges and parameters setting forth the broad scope of the subject matter presented herein are approximations, the numerical values set forth in the specific examples are reported as precisely as possible. Any numerical values, however, inherently contain certain errors necessarily resulting from the standard deviation found in their respective testing measurements.

General Description

The embodiments described herein are contemplated to provide optical interrogation of samples, such as, but not limited to, solids, soft solids, and liquids that include oil-based samples. The length of the transmission path of the light through a given sample varies over a wide range depending on the given sample and the type of measurement that is needed. The present embodiments described herein are thus designed to provide the user with a high degree of control over one or more path lengths in real time and automatically. The beneficial result of such a novel aspect is that by collecting and storing many data sets of different path lengths automatically, later analysis of the stored data collected is possible at many different path lengths.

Another beneficial aspect of the embodiments described herein is that the configuration also provides an easy means to allow the user to place a small sample (typically a drop of a sample on a sampling window in the light beam for analysis, which naturally allows for the easy removal and cleaning of the sample from the sample cell windows to enable rapid analysis of many samples in a short amount of time.

Specific Description

Turning now to the drawings, the apparatus, as illustrated in FIG. 1 and generally designated by the reference numeral 100, shows a rotational arm configured to be in an "open" position in which a sample of a solid (soft pliable samples) (not shown or reference solid sample can be applied or a drop of analyte or reference sample (not shown), (e.g., samples of less than about 2 μl, oil based samples, liquid samples,), can be dispensed or aspirated onto a lower surface of a configured window 5'. As discussed in more detail below, such an "open" position enables easy access to the ends of the surfaces, e.g., desired surface configurations for optical windows 5 and 5', so as to apply any of the given samples and enable a user to easily clean such surfaces provided on windows 5 and 5', and to mount a new sample within the apparatus when desired.

Thereafter, upon the application of a sample, the arm 4 of apparatus 100, as shown in FIG. 1, is angularly moved by a user to be in the "Operating", i.e., closed position (as often sensed by position sensor (not shown)), an as to result in the desired surface of window 5 to be brought into contact with a desired sample contained therebetween surfaces provided by windows 5 and 5'. Such a configuration enables, such as, but not limited to, a surface tension mode (i.e., pulling sample into a column) or a mode that enables "squeezing" the sample via the configured surfaces of windows 5 and 5'. In either of these example modes, it is to be appreciated that the apparatus 100 shown in FIG. 1 can thereafter, as described hereinafter, collect and store many data sets of different path lengths automatically and thus provide later analysis of the stored data at the many, if needed, different path lengths.

Turning back to FIG. 1, the closed. "Operating" position is aided by the mechanical coupling of a hinge rod 6 configured therethrough bores in both the swing arm 4 and in a hinge spacer block 6', with hinge spacer block 6' being rigidly fixed with respect to base plate 2. In addition, a detector casing 7, which can include, but is not strictly limited to, a light detector 7 and window 5 coupled to swing arm 4, also must necessarily rotate about hinge rod 6 to enable a surface of window 5 to come into contact with a sample provided on an upper surface of window 5'. It must be noted however, that while samples can often be provided on the upper surface of lower window 5, it is to also be appreciated that given samples can also be applied to the lower surface of upper window 5 in some instances. If that is the desired mode of operation, the sample is then angularly rotated via arm 4 to come into contact with the desired surface of lower window 5' without departing from the working embodiments described herein.

The present embodiments thus allow the user to easily change from one sample to a different sample by having a moveable pair of windows (5 and 5') that pass a broad range of light wavelengths. Such windows 5, 5' allow a wide range of liquids (e.g., oils) and some solids to be placed into a light beam for spectral analysis. These windows 5, 5' are arranged in an opposing manner. Moreover, the lower window 5' is often bonded to a large flat surface (e.g., sample platform 3) to present the user with a sufficient area that can support samples that can vary in size and type. The upper window 5 can be bonded to the aforementioned moveable arm 4 that can be raised e.g., rotated away) to allow the placement or removal of a sample and then lowered to the sample to collect spectral data. The sample can, as an example, be a thin pliable solid but is typically a liquid as such a media allows the path length to be varied and is therefore a desirable sample type although the apparatus shown in FIG. 1 and as described herein can of course accommodate non-liquid samples as well.

Figure 2:
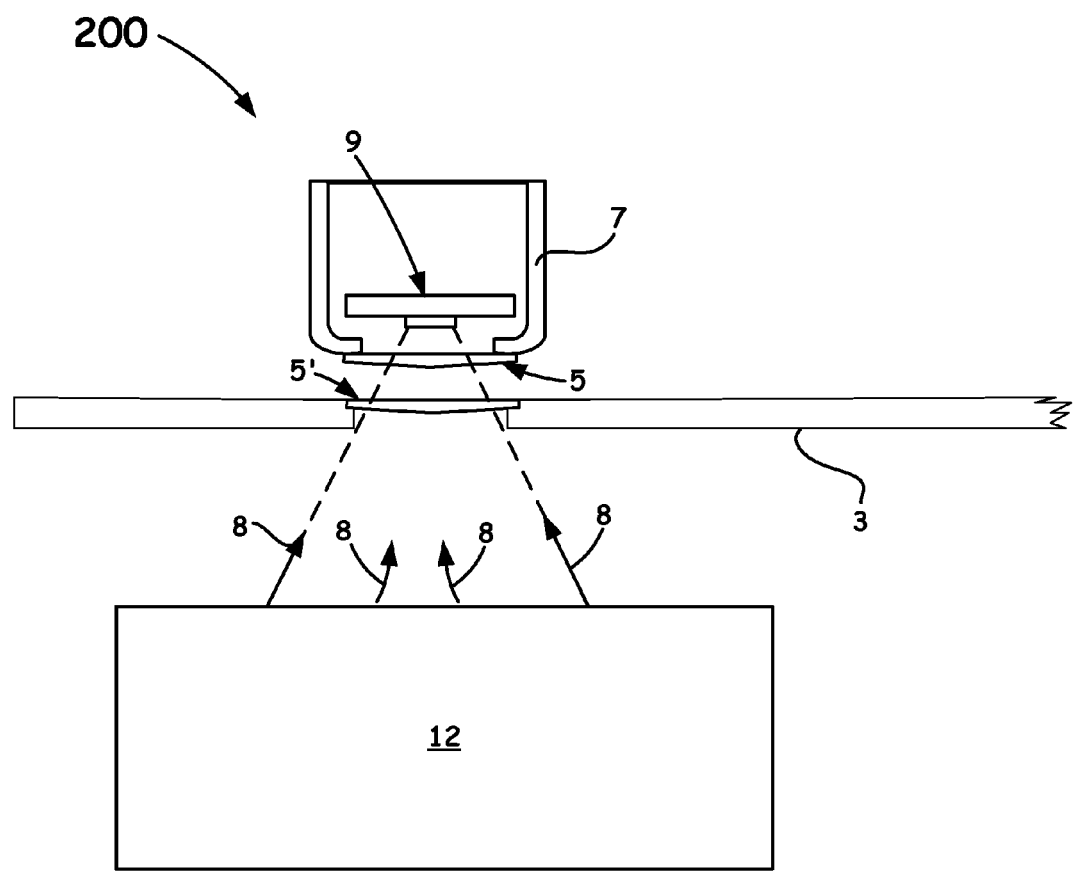
FIG. 2 shows an exploded view of the optical mechanical components used to provide IR transmission measurements.

As an example design for illustrations purposes only, if the field of view of the detector 9, as shown in FIG. 2, is about 45 degrees either side of vertical then the diameter of the lower window 5' is often 2 times the total distance from the bottom of the lower window 5' to the detector 9, which is mounted above the upper window 5. In a desired resultant design, this distance would be 1000 microns for the space from the detector to the upper window plus 200 microns for each window thickness and 500 microns for the normal maximum distance between the two windows. This adds up to 1900 microns times 2, or a minimum lower window size of about 4000 microns.

Using such parameters, a resultant configuration provides for two windows that are at least 4000 microns (4 millimeters (mm)) but preferably 5000 microns (5 mm) to give an adequate area to bond the window at their edges and additionally have dimensions that are easy and low cost to manufacture. Smaller windows can still be used but the use of smaller windows can result in a reduction of the light level reaching the detector 9.

The detector 9 is often but not necessarily coupled (e.g., integrated, incorporated) to the upper window 5 because it is desirably small and light weight allowing the arm to be easily lifted so that the user can clean and inspect the windows quickly. Example infrared (IR) detectors that can be implemented herein include, but are not limited to, deuterated triglycine sulfate detector (dTGS), Lithium tantalate (LiTaO$_3$), Triglycine sulfate (TGS), Indium gallium arsenide (InGaAs), Germanium (Ge), lead sulfide (PbS), Indium antimonide (InSb), Mercury cadmium telluride (MCT), and Mercury zinc telluride (MZT) detectors.

The upper arm 4, as shown in FIG. 1, is designed so that it is easy to lift and swing (rotate) back to a position where the user can easily see the bottom surface of the upper window 5. The arm 4 and window/detector assembly has an upper position (e.g., the "Open" position as shown in FIG. 1) wherein it is held in place by a resilient mechanism (not shown) (e.g., a spring), or a magnetic means (e.g., an electromagnetic or permanent magnet), so that the user can use both hands to clean and inspect the upper window. At the same time the lower window 5' is operationally uncovered so that the lower window 5' can also be easily cleaned and inspected.

The light source 12 can be configured from a number of known designs, such as, but not limited to an incandescent lamp, an ionized gas lamp, a laser, a light emitting diode, etc. to provide desired electromagnetic radiation. Preferably, the source 12 is configured to provide the optical energy over free space to a desired optical window described herein (e.g., a lower window 5'). The optical bandwidth provided by the source 12 can be over any desired wide range of wavelengths or narrow bands of wavelengths but often the source is designed to provide infrared light from about 1 micron up to about 25 microns. As is often desired, such IR light can be modulated for Fourier transform infrared spectroscopy (FTIR) interrogation. In addition, such IR sources, often being larger and especially when coupled to desired optical focusing means (not shown) are thus designed to be located below and/or to the side of the lower window 5'. Such components can however, be designed to move but are often designed to be fixed for convenience.

The sample arm 4 has a repeatable mechanical stop, e.g., in the form of pin (not shown) or hinge 11, that provides a desired position against which the lower surface of the arm 4 abuts when the arm is rotated so as to provide for the contact and measurement of a sample. Such a configuration provides for a repeatable down (active) position relative to the light source optics which directs the upward traveling light (see reference characters 8) towards a repeatable dimensional location (e.g., a focal point). This is the same repeatable location that the detector 9 has when the sampling arm 4 is in the lower position, as shown in FIG. 1. As discussed above, a resilient mechanism, e.g., a spring, or a magnetic means, e.g., electromagnetic or permanent magnet, can be used to provide extra force to holding down the sampling arm 4 in a repeatable location as the data collection is done.

FIG. 2 shows a more detailed view of the transmission cell section of the optical arrangement and is now referenced to provide clarity of the embodiments herein. Thus, FIG. 2 shows a disclosed arrangement, generally designated by the reference numeral 200 that includes a sample platform 3, the respective upper and lower windows 5 and 5', the detector case 7, and detector 9. Also generally shown is an optical source 12, often an IR optical source, and even more often an IR source to provide a modulated IR beam for FTIR as known to those of ordinary skill in the art, as briefly discussed above. However, while FTIR is a desired embodiment so as to operate in the near-infrared as well as the mid-infrared regions, it is to be appreciated that the present configurations can also be configured with other near-infrared to mid-infrared spectroscopic systems and should not be construed to be limited to FTIR systems solely.

Turning back to FIG. 2, a resultant transmission cell is shown having a plurality (often two) of windows 5 and 5', often thin diamond windows, configured with special surfaces (to be discussed below) and an adjustable mechanism 14 (e.g., a motorized (stepper-motor)), which is coupled to sample platform 3 (as shown FIG. 1), adjust the space between (i.e., to adjust optical path lengths) the two windows 5 and 5' (also to be discussed in detail below). From such a configuration, adjustable lengths over the range of about 10 microns up to 1000 microns are provided by the system shown in FIG. 1.

Again referring to FIG. 2, as an example mode of operation, the light beam typically travels vertically up or down through the windows 5 and 5' but can travel at other angles if desired by the user through software or manual control. Since the light detecting means (e.g., detector 9) are typically smaller than the light sourcing means (e.g., light source 12), the light is normally directed up (see reference characters 8 and denoted accompanying directional arrows) toward the detection means (e.g., detector 9) to allow the design of the small light weight detector 9 to move with the upper window 5 in the sample arm 4 that travels or swings up and or away from the lower window 5' where the light enters the contained sample. This moveable detector via mounting arm 4 allows both the upper and lower windows 5, 5' to be accessible for both loading new samples and cleaning any old samples that might be adhering to either upper or lower sample windows 5, 5'.

The light detector 9 incorporated is often designed to be substantially small dimensionally not only to operate at sample temperature but to also beneficially place the detector 9 very close to the upper window 5 in the moveable arm 4 and use proximity focusing as a mode to eliminate the need for detector focusing optics. As an alternative arrangement, if the detector 9 operates at a different temperature than the interrogated sample, the example embodiments provided herein enable detector transfer optics (not shown) to be incorporated to allow the detector 9 to be farther away from the sample in a known fashion. A simple elliptical mirror, for example, can be utilized to enable placing the detector 9 father from the sample to allow heating or cooling the sample to temperatures that the detector 9 cannot tolerate otherwise.

The light path through the transmission sampling system originates from a light source means 12 (e.g., an IR light source, such as a modulated IR source), which can include one or more light sources and fixed or variable filtering means (not shown) to create a light source 12 that contains both light intensity and light wavelength information. The light from the source 12 is directed to a focusing means that can include any known configuration of refractive, reflective components that can operationally direct the light through the first window e.g., lower window 5') supporting the sample and then therethrough the second window (e.g., upper window 5), so as to be collected by a light detection means (e.g., detector 9). It is to be appreciated that it is possible in some cases that part or all of the wavelength filtering means (not shown) can be placed in the light path after the sample and windows 5, 5'. However, while the above configuration is beneficial, a more desired optical configuration is to have the light source 12, variable filtering/interferometer and focusing means (not shown), which are typically larger than the light detection means placed near or under the sampling window 5. Thus, the light created is focused in a upward direction through the windows 5, 5' and sample onto a light detection means 9 that is in a known standard location relative to the light source 12 and focusing means that is known to those skilled in the art (not shown). Moreover, it is to also be appreciated that while FIG. 1 shows the apparatus having light source 12 under platform 3 as coupled to window 5' and the light detection means 9 (e.g., photometric or spectrophotometric radiation detector) coupled to arm 4, it is to be stressed that another example embodiment can include arm 4 being configured with the light source 12 (e.g., a photometric or spectrophotometric source) and the platform 3 arranged with light detection means 9 (e.g., photometric or spectrophotometric radiation detector).

It is to be appreciated however that since the light detector 9 is often smaller in a desired fashion than the light source 12, as discussed above, it is thus convenient to place the light detector 9 near the upper sample window 5 in the illustrated moveable arm 4 that can be lifted up and away from the lower sample window to facilitate the user's access to the sample location. This allows the user to inspect both windows so that the user can know that the windows are clean and ready to accept a sample.

As a benefit of this arrangement, the user can, if desired, lower the inspected clean/cleaned upper window 5 and light detector 9 to the standard known location of the apparatus 100, as shown in FIG. 1, to collect a standard "Background" spectrum with no sample in place to verify the entire spectrometer system and to store a reference background spectrum for later use. It is to be appreciated however that it is also possible with many samples to eliminate the background data collection step and just use a Beers law and mathematical model to extrapolate over many different path lengths to build a background spectrum of virtual zero path length, as to be discussed below. In any event, the user can then raise the up window 5 and easily place a sample onto the lower window 5'.

As another example beneficial and novel embodiment, window 5' can be lowered by a computer (processor) controlled motor (e.g., see reference character 14 of motor, as shown in FIG. 1) approximately, for example, by up to 1 millimeter to increase the sample path length before the upper window 5 is lowered to its standard sampling location. This allows the path length to be shortened (i.e., squeezed) as data collection proceeds. This example process of "squeezing the sample" allows high viscosity samples to be run without worry that air introduced into the light beam as the windows 5, 5' are separated.

Maintaining the light detector 9 and window 5 in a known location relative to the light source 12 is important so that a given optical path length between the upper window 5 and lower window 5' can be determined with confidence about the acquired data and stored with the spectral data. In essence, the detector 9 and window location placement enables the changes in sample type and thickness to be measured without concern that the directed light (e.g., the focus of the light beam) has changed due to changes in the detector 9 location relative to the light source optics (e.g., focusing means (not shown)). This is important because relative motion between the light source optics (not shown) and an example light detector 9 can cause a change in the amount of the light collected by the detector 9 and if left unchecked, produce an erroneous change in apparent light absorption of the sample if the detector location changes between different sample and background reference data collection scans.

Therefore the upper sample window 5 and detector 9 are often, but not necessarily, only moved to two repeatable positions in the present embodiments. The up position allows the users to remove, clean, inspect, and place samples on the sample windows, and the down provides a fixed focus and known optical path length during the collection of background (no sample reference) and sample scans.

Turning, back to FIG. 1, lower sample window 5' is coupled (e.g., via bonding) to a flat sampling platform 3. It is to be appreciated that either of the windows 5, 5' and/or alternatively, the sample platform 3 can be treated with a material (e.g., a hydrophobic, a hydrophilic coating) known by those of ordinary skill in the art to prevent over spreading of an applied liquid drop analyte (e.g., oil) or reference sample (e.g., to stop spreading of an applied sample at the confines of the sample platform 3). The platform 3 design itself however, is also configured to prevent any liquid sample from running away from the sample window(s) 5, 5' location and dripping over the edge of the sampling platform 3 into the supporting mechanism and optics below the sample window(s), 5, 5' and platform 3. Moreover, such a large platform 3 enables many different samples to be placed between the windows 5, 5'. To further prevent leaking of the sample (not shown), the sample platform 3 is often of solid construction and has no perforations (e.g., holes, slits, etc.) where a desired sample can flow or leak down under the sample platform 3. As an added arrangement, the sampling platform 3 surface can be, but not necessarily, surrounded by a lip or wall to contain liquid samples if large amounts of sample were accidentally placed in the sampling area.

As another feature, the sampling platform 3 can also be mounted on a hinge if the hinge is a large distance (e.g., at least 60 millimeters) from the window to limit the angle of tilt as the window is raised and lowered. This fact also allows a single piece of stainless steel to act as the sample platform 3 to hold the lower window 5'. This single part can be fixidly mounted to the base of the system if more than 60 millimeters away from the window. Another arrangement includes the use of a thin flexible surface platform 3. In particular, the natural flex in a thin piece of metal, such as, but not limited to stainless steel, can operate as a hinge, with a benefit that there are no gaps for liquid samples to leak though the hinge area down into the light source means and other mechanism mounted underneath the same sample platform 3.

The sample platform 3 is also capable of being mounted on (i.e., coupled to) the adjustable mechanism 14 (e.g., a computer controlled elevator, such as, a motorized (stepper-motor)), for the purpose of varying the sample path length between the two sample windows. Such an adjustable mechanism 14, (e.g., a motor can be controlled by a manual switch or by a computer program. A preferred embodiment of the invention is however, software controlled motor 14 that can automatically vary the distance between the sample windows to control the light path length through the sample in a programmed way to facilitate the measurement of the absorption spectra of many different samples.

As shown in FIG. 1, the adjustable mechanism 14 can, as one beneficial configuration, include a linear actuator 16 with, for example a motor configured as the adjustable mechanism 14 secured to the base plate 2 by means of fasteners, such as, for example, screws, posts, pins, rivets, etc. The use of a motor 14 in such an arrangement thus provides a rotational motion of the linear actuator 16 to cause lift to or to lower the sample platform 3. Preferably, the travel distance and/or position of the linear actuator 16 or any elevator/lowering, means incorporated is monitored during operation of the apparatus 100, as shown in FIG. 1. As an added arrangement, movement of the motor 14 and/or platform 3 can include a reference position sensor (not shown) that establishes a "home" or reference position when the motor control system initializes upon startup or interrupted by, for example, an opto-interrupter device (not shown).

Through such a motor/software controlled arrangement, the entire sample platform 3 can thus be moved up and down, for example, by about 500 microns up to about 1000 microns to change the sample path length as needed. In a desired embodiment, the lower sample window 5' via coupling to the sample platform 3 can be programmed to stay in the lower location so that the user can clean, inspect and collect background data. Only after a sample is loaded and data collection is started is the program going to move, e.g., raise the sample window 5'/platform 3 to reduce optical path length as needed.

The sample platform 3 can thus be programmed to stay in the lower position all the time until the sample arm 4 is lowered to protect, for example, configured diamond windows 5, 5' from damage caused by the sample arm 4 being inadvertently forced down rapidly. In particular, such a rapid and inadvertent movement can, if not prevented, enable hitting the stop with enough speed and force to bend/deflect the arm 4 and support systems enough to force example configured diamond windows 5, 5' together with enough force to damage them. Thus, a desired method of the present application is to provide that only after the sample arm 4 is lowered, into a sampling position is the motor drive enabled to direct the sample platform 3 up to produce small optical path lengths. However, as soon as the arm 4 is lifted, the motor 14 drive is directed to lower the sample platform 3 enough (e.g., lowered up to 1000 microns) to make damage unlikely.

It is to be noted that with most samples it is possible to first raise and then lower the sample platform 3 a plurality of times with window and surface tension nonetheless keeping a liquid sample in place. Only high viscosity semi-solid samples are limited to a squeeze only to avoid air bubbles. It is also to be noted that the present embodiments described herein are designed to provide surface tension modifying coatings to be added to the sample platform 3 to aid in keeping the sample on the window rather the spreading out on the sample platform 3. These coatings allow the same sample to be run at different path lengths over a number of repeated data collection cycles and aid in the use of low viscosity samples. Different coatings are thus used with different types of samples to aid the user in quickly and accurately placing a sample on the lower window 5'.

Turning back to FIG. 2, the windows 5 and 5', which can be coated (e.g., anti-reflection (AR) coated) on desired surfaces to increase light throughput, are mounted above and below each other. The light 8 travels up from the light source via configured optics (not shown) that are below the lower window 5' to detector 9 which is mounted as close as is reasonably possible to the upper window 5. By placing the detector very close to the upper window (e.g. to within microns) the need for any optics between the detector and the upper window is eliminated. In a desired arrangement, the upper window 5 is a diamond window of about 200 microns thick although window 5 is not limited to just such a thickness. The detector 9 is mounted at about 1000 microns up to above 500 microns above the upper window 5. The lower window 5' is also often but not necessarily a diamond window of about, but not necessarily 200 microns thick. Thin windows, when diamond is the material, are important to reduce cost, reduce diamond phonon absorption, and to reduce distance from the detector to the bottom surface of bottom window but again, the present embodiments described herein are not to be limited to just thin windows.

The preferred windows have a flat side, and a side with a conic (e.g., cone) shaped surface, as somewhat depicted in FIG. 2, wherein the center of the window (e.g., 5) is thicker (at about 200 microns) than the edge of the window (at about 180 microns). This feature is desired to allow the center of the window to have a minimum path length even if the window is slightly misaligned (tilted) in manufacturing. Such a cone shaped feature also reduces spectral "channeling" caused by light reflecting from one flat surface of a sampling window to a second flat window surface. These reflections can cause trouble if they occur inside the window (between the front and back surface of a single window) or if they occur between any two different windows surfaces if they are flat and next to each other. Therefore each window has one flat and one cone shaped window. These windows can be used with the cone facing up or down. The preferred window set up is with the flat surface of the detector window up towards the detector and the cone pointing down toward the sample. The bottom window has the flat surface pointing up toward the sample and the bottom side of the lower window has a cone shaped face pointing down toward the light source. Therefore the up cone shape face of the upper window 5 prevents bad "channel spectral features" from reflections inside the upper window surfaces and from the airspace between upper and lower windows where the sample is placed. In addition, it is to be appreciated that the lower window 5' cone facing downward prevents bad channel spectra feature from the reflections inside the lower window itself.

As a preferred embodiment, a desired application herein is to provide that only the lower window moves as data is collected to change path lengths. The upper window, detector and the source optics thus preferably, but not necessarily, do not move as data is collected to provide the best possible stability in absorption measurements. Thus, moving only the lower window (e.g., moving between about 10 to 1000 microns) to produce the optical path length changes allows the design of the motorized lower window drive system to be smaller, more rigid, more repeatable, and lower in cost. The motorized drive system (i.e., adjustable mechanism 14) needs to move the lower window 5' up and down in a repeatable way with long term accuracy of only a few microns. Getting enough resolution in the drive system to have the ability to move less than one micron per control step is not that difficult using current systems known to those skilled in the art. However, despite such current systems, there is still a need to calibrate the zero point where the windows touch and the optical path length is a minimum in field so that the user can trust the measurement. Such a calibration step provides confidence to the user that the windows 5 and 5', as shown by the closed "operating" position in FIG. 1, touch (the minimum optical path length) so as to take into account normal wear, corrosion and temperature changes in the mechanical stop and hinge assembly of the detector arm 4.

This zero calibration can be done by several means. One is to place a liquid (e.g., water or alcohol) sample in the transmission cell and to measure the optical absorption as the windows are driven toward minimum optical path length. If the absorption is measured every step of the travel movement, the absorption will change (decrease) each step until the windows touch, then the absorption changes that were monitored suddenly decreases greatly. This sudden change in absorbance change per step thus indicates the point at which minimum path length occurs.

Another method to calibrate optical path length is to measure the small amount of optical channel spectra detectable with windows, such as the windows described herein, of which are designed to ultimately remove the channel spectra with samples but not completely with air. This optical channel signal is weak by design but it is a very accurate measure of the optical path length between the two windows if signals are averaged over an adequate amount of time, e.g., at about 60 seconds or longer. Such a method is beneficial in that the procedure can measure non zero path lengths out to about 50 or more microns with excellent accuracy allowing not only the zero point to be measured but also all the shorter path lengths.

As another beneficial alternative, a good zero calibration point method that is designed to be faster than the aforementioned process is to insulate one of the mechanical stops and measure the sample arm stop contact resistance electronically (i.e., a current measurement system). As the path length decreases to zero the windows touch and the arm is lifted off the stop and the resistance of the stop contact jumps up. This can be measured on every sample run with very little or no added time.

Data Control System

It is to be appreciated that the method of operation or various selected steps thereof, can be carried out automatically by a system including a computer or other electronic processor and computer program instructions tangibly embodied on a computer readable medium, such as a disk drive, magnetic tape, optical disk drive, memory card, etc. The computer readable medium may perform as both an input and an output device. Optionally, the computer/processor may further be electronically coupled to one or more other output devices, such as display screens, printers, etc. and/or one or more other input devices, such as keyboards, internet connections, etc.

In the system 100, the computer/processor (not shown) in an example arrangement provides instructions to set the path length(s) for the sample therebetween the windows 5, 5' to a certain value(s). For example, the computer/processor may automatically send instructions to set or change path lengths and collect optical information from interrogated samples manipulated to provide various path lengths. If the system of FIG. 1 also includes a position sensor, such position information may be returned to the computer processor to provide path length adjustments. The computer processor (not shown) also receives electronic signal information from the light detector 9 relating to the intensity (e.g., power) of light sensed by the light detector 9 after transfer of such light from the transmission cell section of FIG. 1, as described above. The computer/processor may also automatically perform the calculations and evaluate the decisions provided by for example, software, graphical user input (GUI), etc., so as to direct steps configured to guide a user. The computer processor (not shown) can also set the values of variables. The sequence of events performed by the computer/processor may be controlled in accordance with program instructions stored on the computer readable medium and transferred to the computer/processor therefrom. Results of the measurements may also be transferred from the computer/processor to the computer readable medium for storage thereon. Output may also be provided to a user via output devices. The user may control program execution via input devices known to those skilled in the art.

A preferred data collection control program method can be configured to operate in the following way. First, the user cart tell the program that new data collection is to be implemented. The program then prompts the user to inspect and clean the windows, if needed. Then the user can lower the upper window and detector arm to the standard sampling location and the arm mechanism would signal the computer program that the arm is in the proper location for data collection to begin. The program then signals the user that it is automatically collecting a background spectrum. This spectrum can then be automatically analyzed to see if the light collected had the expected characteristics, indicating that the window(s) 5, 5' are clean and all is OK.

The user then can be prompted to raise the sample window detector arm 4 and place a sample on the lower sample window 5' (and optionally enter a name for next sample to be run). Upon verification, for example, by a position sensor (not shown) that the arm 4 has been raised and lowered the arm in a pattern that indicated that a sample was in place, the control program can then automatically start the data collection cycle.

Data can be first collected with a large space between the sample windows (or large optical path length). The motor is then directed (e.g., via software to include graphical user input (GUI) by a user, etc.) to raise the lower window 5' to reduce the window spacing and path length and then collect more data. This process can be repeated a programmed number of times. As each set of data is collected data analysis can be started on the prior set of data.

The first analysis can be to check for the expected reductions in sample absorbance of the transmitted light. If the absorbance did not proceed according to Beers law the program can provide a signal to the user that there were likely air bubbles in the light beam and to check for a misplaced or undersized sample between the sample windows 5, 5'. As the programmed data collections take place, the program can then present the data to the user who can interpret the data any number of ways. The user can then manually pick the best path length, or run a program that automatically analyzes the data, etc.

As stated above, it is also possible with many samples to eliminate the background data collection and just use a Beers law and mathematical model to interpolate over many different path lengths to build a background spectrum of virtual zero path length which is useful in many data analyses. This technique can lead to time saving when analyzing many samples in a short period of time. Such a differential path length measurement technique is similar to the techniques described in U.S. Pat. Nos. 6,809,826 and 6,628,382.

The fast acting contact resistance position sensing system of the present embodiments also allows sample viscosity measurement as an added feature. The sample window is raised at a constant speed causing the sample thickness to be reduced at a constant speed. At some point the viscosity of the sample spreading out of the decreasing volume will cause enough force on the arm to lift it off of a configured mechanical stop. This can often be indicated by an increase in contact resistance. The force on the sample arm is known, as is the speed of the window movement, and the sample thickness. Knowing these three items thus enables viscosity to be determined over a useful range. This information can be beneficially used to prevent air bubbles from being sucked into the sampling light bean as the path length is increased at too high of velocity in later measurements where the path length is increased.

Control Software Strategy

The user presses a button to start a data collection cycle. The software can then prompt the user to name the sample and to raise and inspect the window for cleanliness. After the windows are cleaned and inspected the user can then label the sample as a background and then lower the sample arm starting the background collect.

The program can use background spectra to verify window cleanness. If this background run is OK the user/or program can store the background for later use. The user can also label the sample and then place the sample into position. In most cases the sample can be a liquid that is placed on the lower window with a pipette. An exemplary sample placed on the window includes one of at least 500 microns thick because of surface tension and viscosity. Therefore in most cases after the user has placed the sample onto the lower window and then lowers the arm onto the sample the sample will then fill the space between the upper and lower windows.

The user can look from the side and see that the sample has in fact filled the space between the windows, but the viewing of the sample in position is difficult as the arm blocks most of the easy viewing angles. Therefore a program can be set up to automatically start collecting data and look for air bubbles from misplaced samples after the arm has been lowered to the standard lower sampling position.

The software can sense that the arm has been lowered, and proceeds in the following illustrative but non-limiting example steps: Step 1) Delay for a programmed time period (about 2 to 15 seconds to allow the detector to settle after the light level change). Step 2) Start data collection for about 5 to 15 seconds. Step 3) Decrease the space (optical path length) between the windows by 50% and collect more data. Step 4) Analyze the data to see that the absorption has decreased by the expected amount of about 50%. If the absorption is not as expected the program could signal the user that there appears to be air in the sample, or too little sample in the window location. Step 5) If the absorption decrease appears to be OK then the program can decrease the spacing (optical path length) by a programmed amount and collect and store a second data set. Step 6) Analyze data again for air bubbles and repeat and collect as many different path lengths as programmed and Step 7) then signal the user that the data collection is complete.

The discussion included in this application is intended to serve as a basic description. Although the present invention has been described in accordance with the various embodiments shown and described, one of ordinary skill in the art will readily recognize that there could be variations to the embodiments and those variations would be within the spirit and scope of the present invention. The reader should be aware that the specific discussion may not explicitly describe all embodiments possible; many alternatives are implicit. Such modifications and the like are considered simple modifications that are well within the ability of one of ordinary skill in the art and within the scope and spirit of the invention. Accordingly, many such modifications may be made by one of ordinary skill in the art without departing from the spirit, scope and essence of the invention. Neither the description, drawings nor the terminology is intended to limit the scope of the invention—the invention is defined by the claims.

The invention claimed is:

1. A method for measuring an optical property of a sample, comprising:
   providing a source of optical energy and a pair of windows; wherein one of the pair of windows is configured to receive radiation from the source of optical energy over free space and the other of the pair of windows is configured with an incorporated optical detector that is utilized to optically interrogate a disposed sample therebetween the pair of windows, wherein the pair of windows are both moveable with respect to the positioning of the source of optical energy to adjust the spacing between them;
   providing a processor adapted to control a separation between configured surfaces of the pair of windows at a variable distance (P) in order to pull the disposed sample into a column contained by surface tension or to squeeze the sample during optical analysis, wherein the processor is additionally configured to collect and store information of different optical path lengths automatically of the pulled and/or squeezed sample(s);
   using the information collected to monitor the expected light absorbance changes as the path length is changed; and
   warning a user that the collected data is likely in error if a measured result varies from an expected Beers law and/or interpolated change rate.

2. A method for measuring an optical property of a sample, comprising:
   providing a source of optical energy and a pair of windows; wherein one of the pair of windows is configured to receive radiation from the source of optical energy over free space and the other of the pair of windows is configured with an incorporated optical detector that is utilized to optically interrogate a disposed sample therebetween the pair of windows, wherein the pair of windows are both moveable with respect to the positioning of the source of optical energy to adjust the spacing between them;
   providing a processor adapted to control a separation between configured surfaces of the pair of windows at a variable distance (P) in order to pull the disposed sample into a column contained by surface tension or to squeeze the sample during optical analysis, wherein the processor is additionally configured to collect and store information of different optical path lengths automatically of the pulled and/or squeezed sample(s);

squeezing the disposed sample between the pair of windows at a fixed rate via a processor controlled motor, wherein as the disposed sample is squeezed thinner, a force needed to squeeze the pair of windows together increases until the force on the pair of windows is high enough to lift a sample loading arm off of a mechanical stop;

processor measuring the time of the sample loading arm lift off of the mechanical stop; and calculating the viscosity of the disposed sample using the speed of the motor, the disposed sample thickness, and the time to provide the force needed to lift the sample loading arm.

* * * * *